(12) United States Patent
Morgan et al.

(10) Patent No.: US 11,382,524 B2
(45) Date of Patent: Jul. 12, 2022

(54) AIRWAY MAINTENANCE DEVICE

(71) Applicants: Nottingham University Hospitals NHS Trust, Nottingham (GB); The University of Nottingham, Nottingham (GB)

(72) Inventors: Stephen P. Morgan, Nottingham (GB); Barrie R. Hayes-Gill, Nottingham (GB); Sergiy Korposh, Nottingham (GB); Ricardo Correia, Nottingham (GB); Jonathan Hardman, Nottingham (GB); Andrew Norris, Nottingham (GB)

(73) Assignees: NOTTINGHAM UNIVERSITY HOSPITALS NHS TRUST, Nottinghamshire (GB); THE UNIVERSITY OF NOTTINGHAM, Nottinghamshire (GB)

( * ) Notice: Subject to any disclaimer, the term of this patent is extended or adjusted under 35 U.S.C. 154(b) by 817 days.

(21) Appl. No.: 15/529,158

(22) PCT Filed: Nov. 20, 2015

(86) PCT No.: PCT/GB2015/053544
§ 371 (c)(1),
(2) Date: May 24, 2017

(87) PCT Pub. No.: WO2016/083782
PCT Pub. Date: Jun. 2, 2016

(65) Prior Publication Data
US 2017/0340216 A1    Nov. 30, 2017

(30) Foreign Application Priority Data
Nov. 25, 2014 (GB) ..................... 1420919

(51) Int. Cl.
  *A61B 5/026*  (2006.01)
  *A61B 5/00*   (2006.01)
  (Continued)

(52) U.S. Cl.
  CPC ........ *A61B 5/0261* (2013.01); *A61B 5/02055* (2013.01); *A61B 5/6885* (2013.01);
  (Continued)

(58) Field of Classification Search
  CPC . A61B 5/0261; A61B 5/02055; A61B 5/6885; A61B 5/027; A61B 5/0285;
  (Continued)

(56) References Cited

U.S. PATENT DOCUMENTS 3,931,822 A    1/1976  Marici
4,886,059 A *  12/1989 Weber .................. A61B 8/12
                                           128/207.15
(Continued)

FOREIGN PATENT DOCUMENTS

CN    203647830 U    6/2014
EP    1281357 A2     2/2003
(Continued)

OTHER PUBLICATIONS

J. E. Spiegel, "Endotracheal Tube Cuffs: Design and Function", Anesthesiology News, Guide to Airway Management, 2010, pp. 51-58.
(Continued)

*Primary Examiner* — Joseph D. Boecker
*Assistant Examiner* — Thomas W Greig
(74) *Attorney, Agent, or Firm* — David D. Brush; Westman, Champlin & Koehler, P.A.

(57) ABSTRACT

The disclosure relates to an airway maintenance device, such as an endotracheal tube, tracheostomy tube, or supraglottic airway device, and in particular to an airway maintenance
(Continued)

device having a sensor for measuring capillary blood flow and/or pressure. The device includes an airway maintenance device with an airway lumen having a proximal end and a distal end, a distal end portion incorporating an optical sensor configured to measure capillary blood flow in tissue surrounding the distal end when in position within a patient's airway. The optical sensor may include a portion of an optical fibre extending to the distal end portion along the lumen.

14 Claims, 9 Drawing Sheets

(51) Int. Cl.
*A61B 5/0205* (2006.01)
*A61M 16/04* (2006.01)

(52) U.S. Cl.
CPC ........ *A61M 16/04* (2013.01); *A61M 16/0402* (2014.02); *A61M 16/0409* (2014.02); *A61M 16/0434* (2013.01); *A61M 16/044* (2013.01); *A61M 16/0456* (2014.02); *A61M 16/0465* (2013.01); *A61M 2205/3306* (2013.01); *A61M 2205/3334* (2013.01); *A61M 2205/3368* (2013.01)

(58) Field of Classification Search
CPC .. A61B 5/0295; A61B 5/026; A61M 16/0402; A61M 16/0409; A61M 16/0434; A61M 2205/3306; A61M 2205/3334; A61M 16/04; A61M 16/0465; A61M 16/0456
See application file for complete search history.

(56) References Cited

U.S. PATENT DOCUMENTS

| | | | | |
|---|---|---|---|---|
| 5,005,573 A * | 4/1991 | Buchanan | ............ | A61B 5/1459 128/207.14 |
| 5,193,544 A * | 3/1993 | Jaffe | ..................... | A61B 5/1459 128/207.14 |
| 5,546,935 A * | 8/1996 | Champeau | ............ | A61M 16/04 128/204.23 |
| RE35,531 E * | 6/1997 | Callaghan | ............. | A61M 16/04 128/200.23 |
| 6,716,178 B1 * | 4/2004 | Kilpatrick | ................ | A61B 5/01 600/342 |
| 6,859,658 B1 * | 2/2005 | Krug | ................... | A61B 5/14552 600/323 |
| 7,128,071 B2 * | 10/2006 | Brain | ..................... | A61M 16/04 128/207.15 |
| 2004/0003814 A1 | 1/2004 | Banner et al. | | |
| 2005/0279360 A1 * | 12/2005 | Wei | ........................ | A61M 16/04 128/207.14 |
| 2006/0094941 A1 * | 5/2006 | Cho | .......................... | A61B 5/01 600/316 |
| 2010/0006103 A1 * | 1/2010 | McGinnis | ............ | A61B 5/1459 128/207.15 |
| 2010/0113916 A1 * | 5/2010 | Kumar | ..................... | A61B 5/06 600/424 |
| 2010/0280362 A1 * | 11/2010 | Li | ............................. | A61B 5/72 600/424 |
| 2011/0030694 A1 | 2/2011 | Schaner et al. | | |
| 2011/0230742 A1 * | 9/2011 | Finneran | ........... | A61M 16/0484 128/207.14 |
| 2012/0089023 A1 * | 4/2012 | Schlager | .............. | A61B 8/0841 600/439 |
| 2012/0089041 A1 | 4/2012 | Schlager | | |
| 2012/0220845 A1 * | 8/2012 | Campbell | ......... | A61M 16/0447 600/364 |
| 2013/0281885 A1 * | 10/2013 | Rowbottom | ...... | A61M 16/0434 600/587 |
| 2014/0180030 A1 * | 6/2014 | Dorando | ................ | A61B 5/026 600/301 |
| 2017/0196478 A1 * | 7/2017 | Hunter | ............... | A61B 5/02055 |

FOREIGN PATENT DOCUMENTS

| | | | | |
|---|---|---|---|---|
| EP | 1974766 A1 | 10/2008 | | |
| GB | 2033575 A | * 5/1980 | ............ | A61B 5/026 |
| GB | 2033575 A | 5/1980 | | |
| WO | 2004030527 A1 | 4/2004 | | |
| WO | 2010108173 A2 | 9/2010 | | |
| WO | 2012082715 A2 | 6/2012 | | |
| WO | WO-2012082715 A2 | * 6/2012 | ........... | A61B 5/0215 |

OTHER PUBLICATIONS

Pneumatikos et al., "Ventilator-associated Pneumonia or Endotracheal Tube-associated Pneumonia?" Anesthesiology 2009; 110:673-80.
J. Brimacombe et al., "Direct measurement of mucosal pressures exerted by cuff and non-cuff portions of tracheal tubes with different cuff volumes and head and neck positions", British Journal of Anaesthesia 82(5): 708-11 (1999).
G.T.G. Knowlson & H.F.M. Basset, "The pressures exerted on the trachea by endotracheal inflatable cuffs", British Journal of Anaesthesia 42, 834-837, 1970.
P. Goethals et al., "A novel airway device with tactile sensing capabilities for verifying correct endotracheal tube placement", J Clin Monit Comput (2014) 28: 179-185.
E. Bick et al., "Fewer sore throats and a better seal: why routine manometry for laryngeal mask airways must become the standard of care", Anaesthesia 2014, pp. 1-5.
International Search Report dated Jan. 20, 2016 for corresponding International Application No. PCT/GB2015/053544, filed Nov. 20, 2015.
Written Opinion of the International Searching Authority dated Jan. 20, 2016 for corresponding International Application No. PCT/GB2015/053544, filed Nov. 20, 2015.
Search Report dated May 26, 2015 for corresponding GB Application No. 1420919.1, filed Nov. 25, 2014.
Exam Report from the European Patent Office dated Jul. 3, 2019 for corresponding European Application No. 15800924.1.

* cited by examiner

AIRWAY MAINTENANCE DEVICE

CROSS-REFERENCE TO RELATED APPLICATIONS

This Application is a Section 371 National Stage Application of International Application No. PCT/GB2015/053544, filed Nov. 20, 2015, which is incorporated by reference in its entirety and published as WO 2016/083782 A1 on Jun. 2, 2016, in English.

FIELD OF THE INVENTION

The invention relates to an airway maintenance device, such as an endotracheal tube, tracheostomy tube, or supraglottic airway device, and in particular to an airway maintenance device having a sensor for measuring capillary blood flow and/or pressure.

BACKGROUND

Airway maintenance devices, such as endotracheal tubes, are integral to critical patient care. Such devices will often include an inflatable cuff to provide a gas seal within the surrounding airway, which, by reducing leakage of gas around the cuff, facilitates mechanical ventilation of the lungs. Forming a reliable fluid seal between the cuff and the airway is also important for preventing flow of infected secretions travelling from the mouth, past the cuff, and into the lungs.

Pressure exerted by an inflatable cuff on the airway wall can in some cases cause ulceration and scarring of the airway. This problem can be compounded by over-inflation of the cuff by medical practitioners. It is not always obvious what pressure will actually be exerted on the airway by the cuff when inflated, which can lead to over- or under-inflation. This is especially true given the unique nature of each patient, some of whom may have a lower threshold for damage by an inflated cuff.

Spiegel [reference 1] outlines the typical ranges of pressures for conventional HVLP (high volume, low pressure) cuffs, which require about 20 cm $H_2O$ (about 2 kPa) to seal the trachea. The pressure limit for cuff inflation is determined in part by the blood pressure of the capillaries supplying the surrounding trachea, which is typically around between 17-28 cm $H_2O$ (1.7 to 2.7 kPa). A contact pressure approaching or exceeding this typical capillary blood pressure will result in decreased blood flow and ultimately total obstruction of blood flow. Over time, this can lead to serious tracheal injury, particularly Post Intubation Tracheal Stenosis (PITS). PITS is probably responsible for around 85% of all cases of acquired tracheal stenosis. In patients ventilated for more than 10 days, around 15% develop PITS, a life threatening and debilitating condition with a protracted course, typically requiring multiple complex surgeries. Conservative estimates of the direct surgical costs resulting from PITS in the UK alone are between £1 M and £2 M per annum.

Recently, the importance of Ventilator Associated Pneumonia (VAP) as a cause of morbidity and mortality and very high healthcare costs has been recognized. VAP is estimated to occur in around 20% of ventilated patients, and increases the length of stay by around 6 days, adding to care costs (estimated to amount to over $1.2 bn p.a. in the US), and increasing mortality by up to 50%. Many interventions have been proposed to reduce its frequency. These focus on three main areas 1) reducing contamination of the upper airway, 2) reducing aspiration of contaminated secretions, and 3) reducing duration of ventilation, but the single most important factor in VAP is the presence of the endotracheal tube.

The increasingly recognized importance of VAP has recently resulted in a raft of new endotracheal tubes being introduced. These include new suction ports and new cuff materials and shapes. However, such empirical design changes can result in only small incremental improvements.

So called High Volume, Low Pressure cuffs were introduced to reduce pressure related injuries. Pneumatikos et al. [reference 2] discuss the effects of inflation of these cuffs. These cuffs create a fair gas seal but the large volume of cuff material results in folding of the material and creation of micro channels potentially allowing infected secretions to reach the lungs. This can cause Ventilator Associated Pneumonia (VAP). It is therefore important to ensure that the right size of cuff is used for the patient, as well as using the correct pressure, but it is not always possible to gauge either of these sufficiently accurately.

Current best practice involves choosing a device (according to physician or institution preference), with a size based on the patient's age/height/sex. The cuff is then inflated to a standard pressure or volume, or until no leak is apparent. All of this is irrespective of the patient's general condition, including the state of their oxygenation and arterial pressure. Following such standard practice can in some cases result in inadvertent harm to the patient that might not be recognised until later on.

Previous attempts have been made to measure the intra-cuff or contact pressure at the distal end of an airway maintenance device, for example as disclosed in US 2012/0089041, US 2011/0030694 or US 2004/0003814 [references 3-5]. However, these devices tend to require wires to power electronic sensors and to return electronic signals from the sensor. Inserting wires into the human body presents regulatory difficulties, and can be potentially very dangerous in patients with, for example, pacemakers installed. The electromagnetic fields created by the wires can interfere with pacemaker operation, with potentially fatal consequences. Additionally, such devices may not be able to provide an accurate determination of contact pressure between a cuff and the surrounding tissue. Measuring the internal pressure of the cuff, whether of the HVLP or LVHP type, does not necessarily provide an indication of the contact pressure, due to the elasticity of the cuff material, although intracuff pressure has been shown experimentally to correlate reasonably well with contact pressure for HVLP cuffs [reference 1]. Providing a pressure sensor to measure contact pressure can, however, add bulk and mass around the cuff and distort the cuff material. Providing a pressure sensor on the outside of the cuff to measure contact pressure can for example create a point contact with the surrounding tissue, thereby creating an artificially high contact pressure as well as a potential point of injury. Measuring pressure alone, or at least via conventional means, does not therefore resolve the problems inherent with conventional airway maintenance devices.

It is an object of the invention to address one or more of the above mentioned problems.

SUMMARY OF THE INVENTION

In accordance with a first aspect of the invention there is provided an airway maintenance device comprising an airway lumen having a proximal end and a distal end, a distal end portion incorporating an optical sensor configured to measure capillary blood flow in tissue surrounding the distal end when in position within a patient's airway. The optical sensor is configured to detect light reflected from tissue surrounding the distal end portion of the airway lumen, which can be used to determine a measure of capillary blood flow.

The distal end portion may comprise an inflatable cuff. In some circumstances, however, a cuff may be absent, for example for use in young children where the airway may be too narrow to accommodate a cuff without overly restricting the airway. In this case, a lumen of appropriate dimensions may be selected, and the capillary blood flow surrounding the distal end of the lumen monitored by the optical sensor to ensure that a correct fit has been obtained.

Impaired blood supply is the most important factor in the development of post-intubation stenosis. Optical monitoring of microcirculation of blood flow in the capillaries surrounding the distal end of the lumen can reduce the risk of injury by allowing the contact pressure, which to some extent controls the capillary blood flow, to be adjusted for individual patients. Additionally, if a cuff is included it may be an "appropriate volume, appropriate pressure" variety if contact pressure can be measured and adjusted. Lower volume cuffs are known to create a better seal than high volume cuffs, and with a reduced possibility of channels being created allowing the passage of fluids, and so further limit the potential for VAP.

In some embodiments the optical sensor comprises a portion of an optical fibre extending to the distal end portion along the lumen, the optical fibre extending either within the lumen wall or along the outer surface. The use of an optical fibre eliminates any potential or actual problems associated with the placement of electrical wires inside a patient.

The optical sensor may comprise a distal end portion of the optical fibre that terminates within the inflatable cuff. The portion of the optical fibre may have a modified cladding such that light passing along the optical fibre from the proximal end exits the optical fibre radially, i.e. through the modified cladding. Alternatively, or additionally, light passing along the fibre may exit the optical fibre from the distal end face of the optical fibre. The portion of the optical fibre may alternatively have a radius of curvature below a minimum bend radius of the optical fibre such that light travelling within the fibre is emitted from the bent portion of the optical fibre. The minimum bend radius, which is defined as the radius below which total internal reflection in the optical fibre is prevented, will vary depending on the type of optical fibre used, but is typically at least a few millimetres. The minimum bend radius may for example be 10 mm or 5 mm. An advantage of using a bent portion to provide the optical emitting or detecting portion of the optical fibre is that no modification is required to the cladding.

The optical sensor may comprise distal end portions of a pair of said optical fibres comprising a first optical fibre having a light emitting portion and a second optical fibre having a light detecting portion. The light emitting and detecting portions may be offset relative to each other along the axis of the lumen and/or around the circumference of the lumen. An optically opaque barrier may be provided between the light emitting and detecting portions, so that light transmitted directly between the portions is prevented from affecting the detected signal.

A reference optical fibre with a reflective end face may be provided. The reference optical fibre can provide a calibration reading of light transmitted along the lumen that allows any changes that are due to the optical fibre to be taken into account when determining a reading from the detection portion.

The airway maintenance device may be an endotracheal tube, a tracheostomy tube or a supraglottic airway device. Although the specific embodiments disclosed herein relate to endotracheal and tracheostomy tubes, similar issues relating to cuff pressure injuries may also occur with other airway devices such as supraglottic airway devices or laryngeal mask airway devices, which sit behind the tongue in the oropharynx (see, for example, Bick et al.: reference 12). Overinflation of cuffs with such devices can cause problems such as nerve injury or tissue swelling that are different to those associated with tracheal injuries, but the solution provided by the invention of providing a measure of capillary blood flow addresses these problems also.

With the device in position in a patient's airway (i.e. within the trachea or oropharynx), light exiting the optical fibre is absorbed by capillary blood in the tissue surrounding the distal end of the lumen. The optical sensor detects how much of the light is absorbed, thereby allowing a determination of the amount of capillary blood present. A particularly useful type of light to detect capillary blood flow is green light, because this has a low penetration depth in tissue and its absorption is therefore a good indication of the amount of blood flow close to the surface, i.e. capillary blood flow.

In accordance with a second aspect of the invention there is provided an apparatus comprising the airway maintenance device of the first aspect and a control unit connectable to the optical sensor, the control unit configured to operate the optical sensor and determine a measure of capillary blood flow from a signal received from the optical sensor. The measure of capillary blood flow may be displayed on the control unit, for example in the form of a relative indication. If the blood flow is shown by the unit to be insufficient, the medical practitioner may then adjust the airway maintenance device, in particular the intracuff volume and pressure, to reduce the pressure exerted on the airway. The control unit may be further configured to connect to an inflation tube connected to the inflatable cuff (if provided) at the distal end of the airway lumen, to inflate the cuff to a set pressure and/or maintain a set pressure within the cuff.

One or more other sensors may also be provided at the distal end portion of the airway lumen for measuring pressure (e.g. intracuff pressure or contact pressure), temperature and/or humidity.

In accordance with a third aspect of the invention there is provided an airway maintenance device comprising an airway lumen having a proximal end and a distal end, a distal end portion having an inflatable cuff incorporating a fibre optic pressure sensor, i.e. a pressure sensor using an optical fibre as a pressure sensing element. The fibre optic pressure sensor may be configured to measure a pressure between the cuff and tissue surrounding the cuff when in position within a patient's airway. To achieve this, the fibre optic pressure sensor may be mounted on an outer surface of the cuff. The fibre optic pressure sensor may alternatively be configured to measure a pressure within the cuff.

The fibre optic pressure sensor may comprise a portion of an optical fibre extending to the distal end portion along the airway lumen. The optical fibre provides a means of relaying signals from the optical fibre pressure sensor. The use of an optical fibre eliminates the problems associated with the use of electrical wires inside of a patient, as well as minimising problems associated with cuff distortion that may arise with other types of pressure sensing devices.

The fibre optic pressure sensor may comprise a portion of the optical fibre at the distal end of the optical fibre. According to one embodiment of the invention, the fibre optic pressure sensor may be a pressure-sensitive fibre Bragg grating (FBG). According to another embodiment of the invention, the fibre optic pressure sensor may comprise a Fabry-Pérot cavity in an optical fibre and a pressure-sensitive membrane attached to an end-face of the optical fibre.

In some embodiments, the inflatable cuff may incorporate a plurality of fibre optic pressure sensors, each fibre optic pressure sensor comprising a portion of an optical fibre extending to the inflatable cuff. Each of the plurality of fibre optic pressure sensors may comprise a portion of the same optical fibre extending to the inflatable cuff. Using a plurality of sensors can increase the sensitivity of the measurement to the pressure in the trachea, and can reduce or eliminate the effect of temperature on pressure measurements.

In some embodiments, the or each fibre optic pressure sensor may be encapsulated in a protective material, for example a polymeric material such as a rubber or an epoxy. Encapsulation of the sensor can be used to increase the sensitivity and robustness of the sensor.

In some embodiments the inflatable cuff may comprise outer and inner cuffs, the inner cuff provided within the outer cuff. The fibre optic pressure sensor may be provided between the inner and outer cuffs. This double cuff approach allows the sensor to be attached in a way that reduces induced strain during cuff inflation, hence making the sensor more sensitive solely to contact pressure during use.

In accordance with a fourth aspect of the invention there is provided an apparatus comprising the airway maintenance device of the third aspect and a control unit connectable to the fibre optic pressure sensor. The control unit is configured to operate the pressure sensor and determine a measure of pressure within or around the cuff from a signal received from the fibre optic pressure sensor. The measure of pressure may be displayed on the control unit, for example in the form of a relative or absolute indication. If the indicated pressure is shown by the unit to be insufficient or excessive, the medical practitioner may adjust the airway maintenance device to reduce or increase the pressure accordingly. The control unit may be further configured to connect to an inflation tube connected to the inflatable cuff at the distal end of the airway lumen, to inflate the cuff to a set pressure, maintain a set pressure within the cuff and/or provide a modulated pressure to the cuff. Modulating the intracuff pressure may further reduce the risk of post-intubation stenosis or other detrimental effects relating to intubation, as it allows capillary blood flow to be re-established periodically. Modulating the pressure within the cuff allows for capillary refill time to be monitored, in addition to capillary blood flow. The pressure may be modulated according to a preset modulation schedule, for example by reducing the pressure in the cuff to a lower level periodically and then raising the pressure to a previous upper level after a preset time period. The preset time period and the upper and lower levels of pressure may be preset on the control unit, as well as a time period between modulations.

Some embodiments of any of the previous aspects of the invention may further comprise a temperature sensor configured to measure temperature when in position in a patient's airway. The temperature sensor may for example be a fibre Bragg grating provided in an optical fibre.

Also disclosed herein is a method of determining capillary blood flow in tracheal tissue surrounding an airway maintenance device according to the first aspect, the method comprising: transmitting light into the tissue from the optical sensor, detecting light reflected from the tissue by the optical sensor; and determining a measure of capillary blood flow in the tissue from the intensity of reflected light.

Also disclosed herein is a method of determining pressure around a distal end portion of an airway maintenance device according to the third aspect, the method comprising: transmitting light along the optical fibre pressure sensor; and determining a measure of pressure from an intensity of reflected light.

DETAILED DESCRIPTION

The invention is described in further detail below by way of example and with reference to the accompanying drawings, in which.

Figure 1:
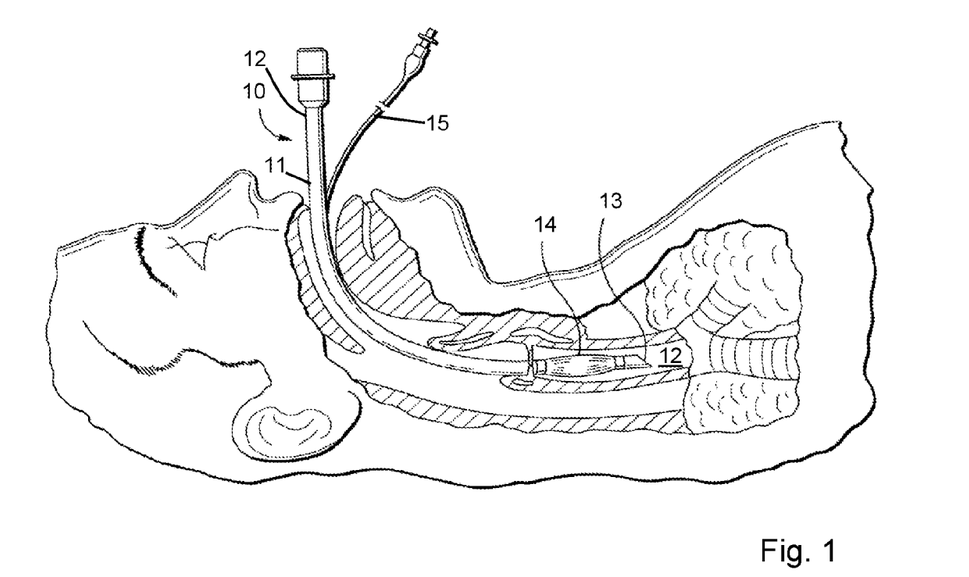
FIG. 1 is a schematic illustration of a conventional airway maintenance device in place within a patient.

FIG. 1 (adapted from reference 3) is a schematic illustration of a conventional airway maintenance device 10, in this case an endotracheal tube, comprising an airway lumen 11 having a proximal end 12 and a distal end 13. The distal end 13 of the airway lumen 11 is indicated in position within a patient's trachea 12. An inflatable cuff 14 is provided at a distal end portion of the lumen 11, the cuff 14 being connected to an inflation line 15 through which fluid (i.e. gas or liquid) can be introduced to inflate the cuff 14 to a desired pressure.

Figure 2:
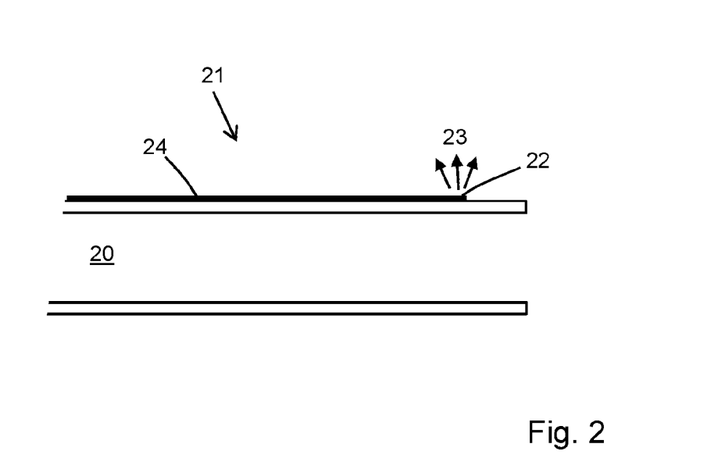
FIG. 2 is a schematic diagram of a distal end portion of an exemplary airway maintenance device.

FIG. 2 illustrates schematically a distal end portion 21 of an exemplary airway maintenance device, on which an optical sensor 22 for measuring blood flow is provided. Light 23 is indicated as being emitted from the optical sensor 22 which, when the airway lumen 20 is in place within a patient's trachea, is directed towards the surrounding tracheal tissue. In a typical embodiment, the optical sensor 22 comprises the distal end of an optical fibre 24, a proximal end of which is connectable to a control unit for providing a light signal to the sensor 22 and for sensing a light signal received from the sensor 22. In alternative embodiments a connection to a control unit may be made by means of electrically conductive wires. An optical fibre connection, however, is generally preferred due to the aforementioned problems involved with inserting electrical wires into a patient.

One or more pairs of optical fibres may be provided along the airway lumen, extending either within or external to the wall of the lumen 20, with a first fibre of each pair providing a light source from a light emitting portion and a second fibre of each pair providing a detector at a light detecting portion for reflected light from the surrounding tissue. The light emitting and light detecting portions of the optical fibres may be at the distal ends of the fibres. The detecting portion may be offset from the emitting portion, so as to minimise direct detection of emitted light. The offset may be axial, i.e. with the emitting and detecting portions at different positions along the axis of the lumen 20. The offset may alternatively, or additionally, be circumferentially offset, i.e. with the emitting and detecting portions at different positions around the circumference of the lumen 20. Any offset between the emitting and detecting portions is preferably greater than around 2 mm. A larger offset results in detection of a higher proportion of light that has penetrated deeper into the surrounding tissue. The emitting and detecting portions may be separated by an optically opaque barrier to prevent light from the emitting portion being received directly by the detecting portion rather than via the surrounding tissue. The optically opaque barrier thereby lowers the background level of light, increasing the signal to noise ratio of the detected signal.

Figure 3A:
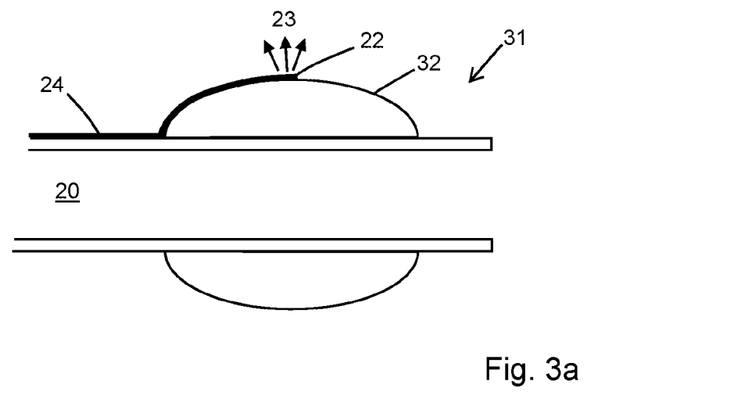
FIG. 3a a schematic diagram of a distal end portion of an alternative exemplary airway maintenance device.
Figure 3B:
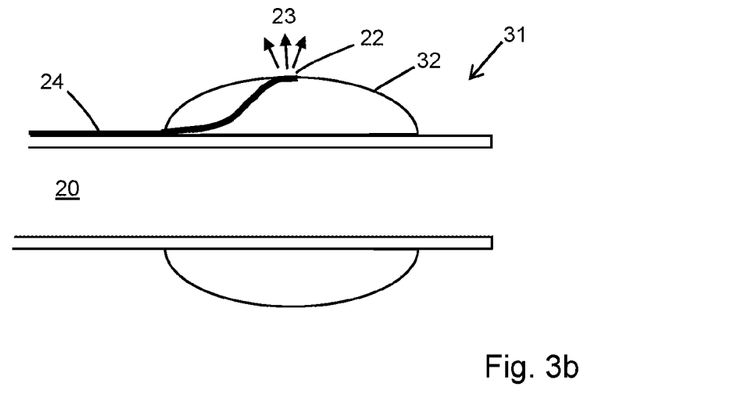
FIG. 3b is a schematic diagram of a distal end portion of a further alternative exemplary airway maintenance device.

FIG. 3a illustrates an embodiment in which the optical blood flow sensor 22 is incorporated into an inflatable cuff 32 on the distal end portion 31 of the airway lumen 20. An inflation tube (not shown), similar to that shown in FIG. 1, is provided for inflating the cuff 32 once the lumen 20 is in place within a patient's trachea. The optical sensor 22 may be mounted on an outer surface of the cuff 32, to allow a direct optical connection with the surrounding tracheal tissue. The optical sensor 22 may alternatively be provided within the inflatable cuff 32, as illustrated in FIG. 3b. This will require the sensor 22 to emit and receive light via the cuff 32, although the effect on readings of capillary blood flow is not expected to be significant. Typical cuff materials are PVC, silicone or polyurethane, all of which can be made transparent to visible light, enabling the optical sensor to function if provided within the cuff. Providing the sensor 22 within the cuff 32 may alleviate issues with the optical fibre 24 providing a restraint on allowing the cuff 32 to expand uniformly when inflated.

Figure 4A:
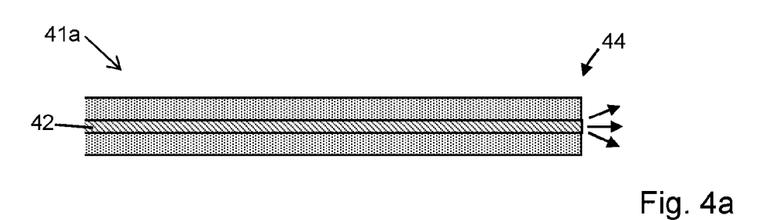
FIG. 4a is a schematic diagram of an optical sensor arrangement.
Figure 4B:
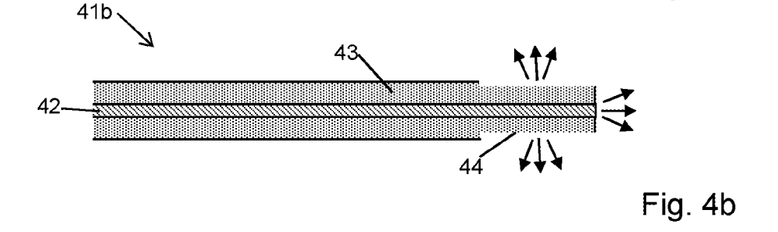
FIG. 4b is a schematic diagram of an alternative optical sensor arrangement.
Figure 4C:
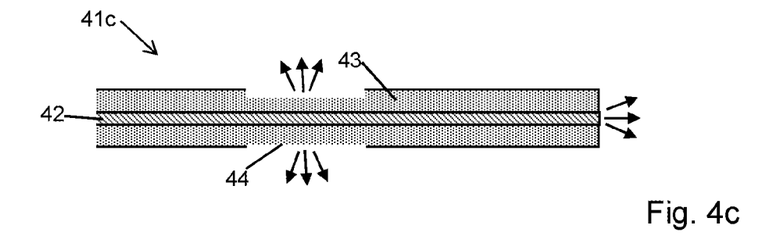
FIG. 4c is a schematic diagram of a further alternative optical sensor arrangement.

FIGS. 4a-d illustrate various alternative configurations for the distal end portion of an optical fibre 41a-d forming the optical sensor as outlined above. In each case, a distal portion 44 of the fibre 41a-d may be used for either emission or detection of light. In FIG. 4a, light carried along the core 42 of the optical fibre 41a exits from the distal end of the fibre 41a. This arrangement, however, results in the emitted light being directed along the axis of the airway lumen, when the direction of light ideally needs to be transverse to the axis, i.e. being emitted in a radial direction with respect to the airway lumen. In the alternative configuration in FIG. 4b, a portion 44 of the cladding 43 of the optical fibre 41b is removed, abraded or otherwise modified to allow light to leak from the fibre in a transverse direction over the portion where the cladding is modified. This alternative arrangement is more suited to providing an optical sensor where light is transmitted into the surrounding tracheal tissue. A further advantage is that the light is transmitted over a more extended region, allowing a greater surface of tracheal tissue to be measured, thereby improving the reliability of the measurement of capillary blood flow. The portion 44 of modified cladding may be positioned further along the optical fibre 41c away from the distal end, as illustrated in FIG. 4c.

Figure 4D:
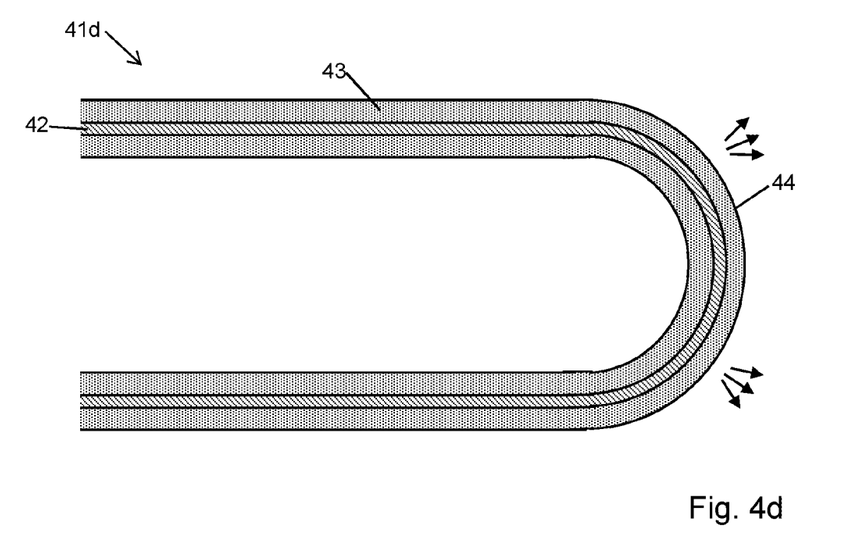
FIG. 4d is a schematic diagram of a further alternative optical sensor arrangement.

In a further alternative arrangement shown in FIG. 4d, the emitting (or detecting) portion 44 of the fibre 41d may be provided by a curved distal portion of the fibre 41d. If the radius of curvature is sufficiently small to prevent total internal reflection within the fibre, light will be emitted from the curved section of the fibre 41d. Conversely, light can be detected in a similarly curved section of fibre.

Light carried by the optical fibre 41a, 41b may be generated from any appropriate source such as a light emitting diode (LED), laser, or other light source. A preferred light source is green light, generally defined as light having a wavelength within the region of 495-570 nm.

Figure 5:
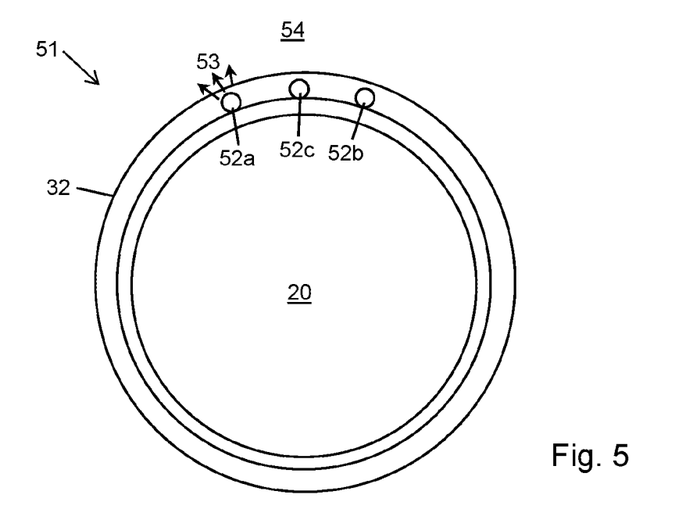
FIG. 5 is a schematic cross-sectional view of a distal end portion of an airway maintenance device.

FIG. 5 illustrates schematically a cross-sectional view of a portion of an airway maintenance device 51 through a distal end portion of the lumen 20. Provided within a cuff 32 are three optical fibres 52a-c. A first optical fibre 52a is provided with a modified portion, for example in the form of one of the alternatives illustrated in FIGS. 4a-d, for emitting light 53 into the surrounding tissue 54. A second optical fibre 52b is provided with a modified portion an offset distance away from the portion of the first fibre 52a for receiving light that has passed through the surrounding tissue 54. An optional third fibre 52c may also be provided for calibration purposes, the third fibre 52c having a reflective end and with no modified portion to emit or detect light. This fibre 52c can be used to correct for any changes in a detected signal that are not due to changes in the surrounding tissue 54 but are instead due for example to bending losses in the fibres 52a-c.

An optically opaque barrier may be provided between the emitting fibre 52a and the detecting fibre 52b. The barrier may for example be in the form of an optically opaque coating on the lumen 20 between the modified portions of the fibres 52a, 52b, which prevents a direct line of sight between the portions. One of both of the fibres may alternatively be provided with a barrier surrounding an inner side facing the lumen 20 so that light is not transmitted directly from the emitting fibre 52a to the detecting fibre 52b.

Figure 6:
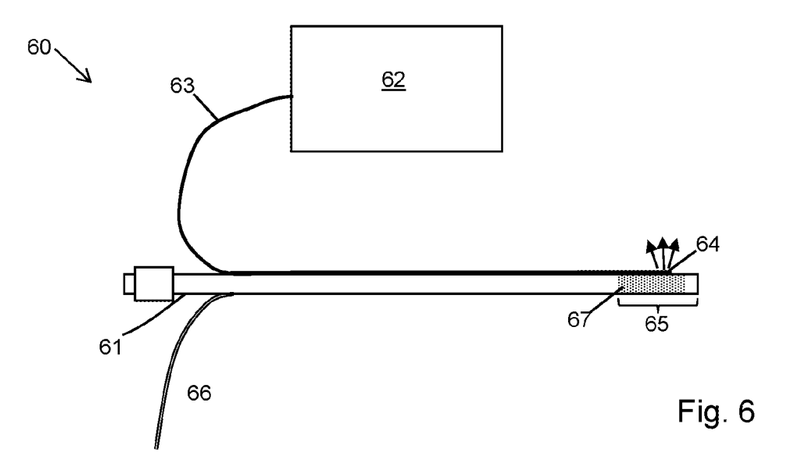
FIG. 6 is a schematic diagram of an exemplary apparatus incorporating a fibre optic sensor.

FIG. 6 illustrates schematically an airway maintenance apparatus 60, comprising an airway maintenance device 61 of the type outline above, together with a control unit 62 connected to an optical fibre bundle 63 for transmitting and receiving light to and from an optical sensor 64 provided at the distal end portion 65 of the airway maintenance device 61. An inflation tube 66 is provided for inflating a cuff 67 provided at the distal end portion 65. As outline above, the cuff 65 is optional in some embodiments. The control unit 62 is configured to determine a measure of capillary blood flow from a signal received from the optical sensor. The intensity of reflected light will vary depending on the amount of capillary blood present in the surrounding tissue. A minimum intensity will be obtained when the contact pressure is a minimum, due to the high absorption of transmitted light by the capillary blood, and a maximum intensity is obtained when the contact pressure is sufficiently high to prevent capillary blood flow, typically at a pressure greater than 30 cm $H_2O$ (about 3 kPa).

The measure of blood flow determined by the optical sensor 64 may be an objective, quantitative measure of the rate of blood flow. Alternatively, the measure of blood flow may be related to a fixed point, for example a known healthy rate of blood flow. Alternatively, the measure of blood flow may be a qualitative measure, i.e. providing a relative indication over time.

The measure of blood flow thus determined may be displayed on the control unit 62, for example in a numerical or graphical format. The information may for example be displayed by means of a graduated scale indicating relative capillary blood flow or capillary refill time, or may be plotted on a display of relative blood flow over time. The control unit 62 contains drive electronics for a light source to transmit light along the optical fibre bundle 63, a photodetector for detecting light received from the optical fibre sensor 64, an amplifier (such as a transimpedance amplifier) for amplifying the detected light signal, an analogue to digital converter and a digital signal processor (such as a field programmable gate array) for processing the amplified signal to produce the required measure. Connections may be provided on the control unit 62 for connection to an external computer, such as via a serial bus or wireless connections such as via a Bluetooth connection.

Impaired blood supply is the most important factor in the development of PITS. By optically monitoring the capillary blood flow as described above, the airway maintenance device 61 may be adjusted to maintain a safe pressure on the tracheal tissue, and so maintain a healthy blood supply while ensuring a good seal between the airway maintenance device and the trachea.

Figure 7:
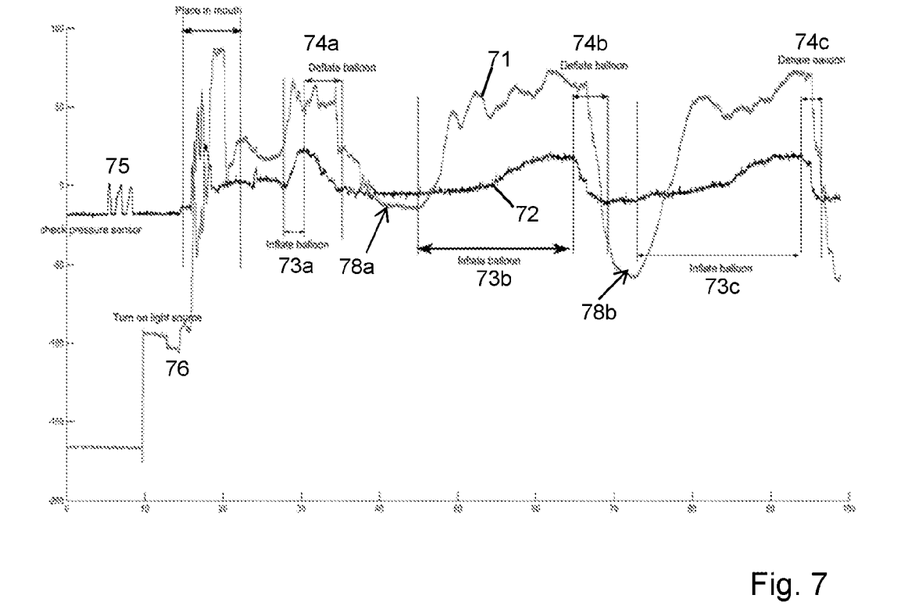
FIG. 7 is a plot of measured pressure and light intensity as function of time for an exemplary device.

FIG. 7 illustrates a plot of reflected light 71 and pressure 72 as a function of time for an exemplary device according to the embodiments described above. A conventional pressure sensor was used to determine contact pressure around the cuff. The plot shows three successive inflations 73a-c and deflations 74a-c, following an initial period involving a check 75 on the pressure sensor, turning on 76 of a light source providing light to the optical sensor and placing 77 of the device (which in this case was in the mouth rather than in the trachea, but the principle is the same). The y axis scales in the plot are dimensionless, indicating only relative pressures and light intensities. As can be seen from the plot, when the pressure increases on inflating the cuff, capillary blood flow is reduced, indicated by an increase in reflected light. As the pressure is reduced, the amount of reflected light decreases as blood returns into the tissue. A fall in pressure followed by a fall in light intensity indicates a hyperaemic response, when blood flow is restored after a period of pressure-induced ischaemia, as indicated at points 78a, 78b.

In further embodiments, one or more additional sensors may be included at the distal end portion of the airway maintenance device, i.e. in a similar location to the optical sensor. The additional sensor or sensors may be configured to measure one or more of pressure, temperature and humidity in or around the airway lumen. An additional sensor may for example be provided to determine a contact pressure between the airway lumen and the surrounding trachea. The contact pressure may be between the device wall itself and the trachea, or between a cuff and the trachea, if a cuff is present. The pressure sensor may also be based on an optical fibre.

Figure 8A:
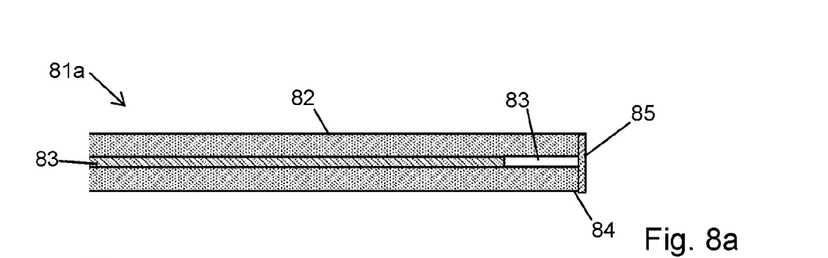
FIG. 8a is an example of a fibre optic pressure sensor based around a Fabry-Perot cavity in an optical fibre.
Figure 8B:
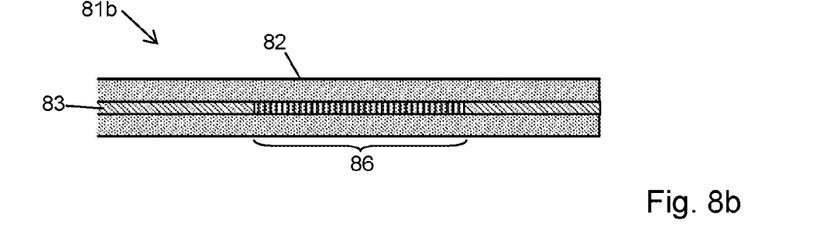
FIG. 8b is an alternative example of a fibre optic pressure sensor based around a fibre Bragg grating in an optical fibre.

FIGS. 8a and 8b illustrate two alternative optical fibre arrangements for providing a pressure sensor as part of an airway maintenance device. The pressure sensor may be provided as an alternative to, or additionally, to the optical sensor for measuring capillary blood flow. In exemplary embodiments, both types of sensors may be provided, since a pressure sensor can provide an indication that the cuff is being inflated while the capillary blood flow sensor provides an indication of whether the pressure is excessive. The optical fibre pressure sensor may be provided in the same or similar configuration to that indicated in FIG. 3 for measuring contact pressure, i.e. on the outer surface of the cuff, or alternatively within the cuff volume for measuring intracuff pressure. The optical fibre pressure sensor may be placed at the longitudinal centre of the cuff, as this is where the maximum pressure will tend to be achieved when in place within a patient's trachea.

FIG. 8a illustrates a first type of fibre optic pressure sensor 81a, based around a Fabry-Pérot cavity. A portion of the core 83 of the optical fibre 82 is removed from the distal end 84, forming a cavity 83. A diaphragm 85 is attached across the end face of the optical fibre 82. Differences in pressure between the cavity 83 and the surrounding environment cause the diaphragm 85 to deflect and change the volume of the cavity 83. This changes the distance that light travels, thereby changing the intensity of light reflected from the end of the cavity 83 due to interference of light from either end of the cavity 83. When the light is in phase at the detector, a high intensity (or bright fringe) is obtained, and when the light is out of phase a low intensity (or dark fringe) is obtained. As the external pressure increases, the intensity of light over a particular range of wavelengths changes, thereby allowing the optical fibre to be used to measure pressure.

FIG. 8b illustrates a second type of fibre optic pressure sensor 81b, which is based around a fibre Bragg grating (FBG). The FBG 86 consists of a periodic modulation of the refractive index of the core 83 of the optical fibre 82. The modulation has a period of the order of the wavelength of light, thereby causing light of that wavelength to be specifically reflected back along the fibre 82. The modulation may be inscribed on the fibre surface or core by ultraviolet light, for example using a high intensity UV laser. A shift in the detected wavelength of reflected light indicates a strain in the fibre 82. The FBG 86 can therefore be used to measure strain directly, or to measure temperature or pressure by the effect such changes have on the FBG 86.

Figure 9:
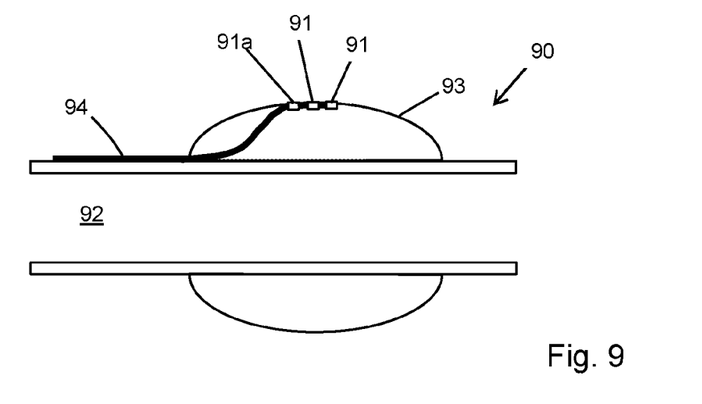
FIG. 9 is a schematic diagram of a distal end portion of a further alternative exemplary airway maintenance device.

FIG. 9 illustrates the distal end portion of an airway maintenance device 90 incorporating a plurality of fibre optic pressure sensors 91a-c. The device 90 comprises a lumen 92 and inflatable cuff 93. Using a plurality of sensors 91a-c can increase the sensitivity of the pressure measurement, and increase the likelihood of at least one sensor coming into contact with the trachea. This is particularly useful if the device is positioned in the trachea such that the pressure sensors 91a-c are near cartilage.

In the illustrated embodiment, fibre optic pressure sensors 91a-c are fibre Bragg gratings similar to the pressure sensor 81b (FIG. 8b), although other embodiments may comprise a plurality of Fabry-Pérot sensors, such as pressure sensor 81a (FIG. 8a). Some embodiments may comprise a mixture of types of fibre optic pressure sensor.

In the illustrated embodiment, each of the fibre optic pressure sensors 91a-c are formed in the same optical fibre 94. In other embodiments, each of the fibre optic pressure sensors 91a-c may be formed in separate optical fibres.

Figure 10:
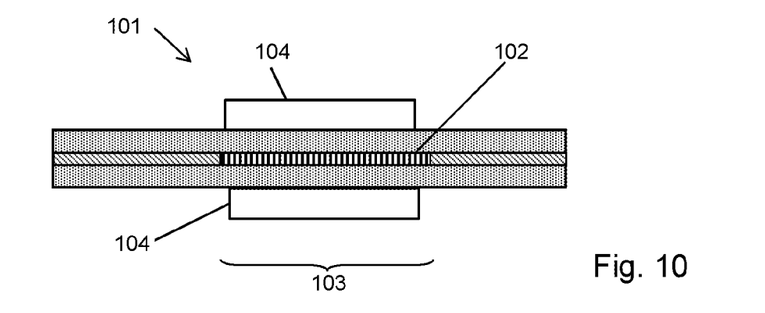
FIG. 10 is an alternative example of a fibre optic pressure sensor based around a fibre Bragg grating in an optical fibre.

FIG. 10 illustrates an alternative embodiment of a fibre Bragg grating optical fibre pressure sensor 101. In this embodiment, the fibre Bragg grating 102 is encapsulated within a patch 103 by embedding the fibre in a protective material 104. The protective material 104 may for example be a polymeric material such as polytetrafluoroethylene (PTFE), rubber, or an epoxy.

Encapsulating the pressure sensor 101 can increase the robustness as well as the pressure sensitivity of the pressure sensor 101. The encapsulation may also reduce or minimise the strain applied to the fibre Bragg grating 102 due to inflation of the cuff, so that the pressure sensor 101 is more sensitive to pressure due to contact with the trachea.

It should be noted that any of the disclosed embodiments of fibre optic pressure sensors may be encapsulated into a patch. In particular, each of the plurality of fibre optic pressure sensors 91a-c, as shown for example in FIG. 9, may be encapsulated into patches.

Figure 11:
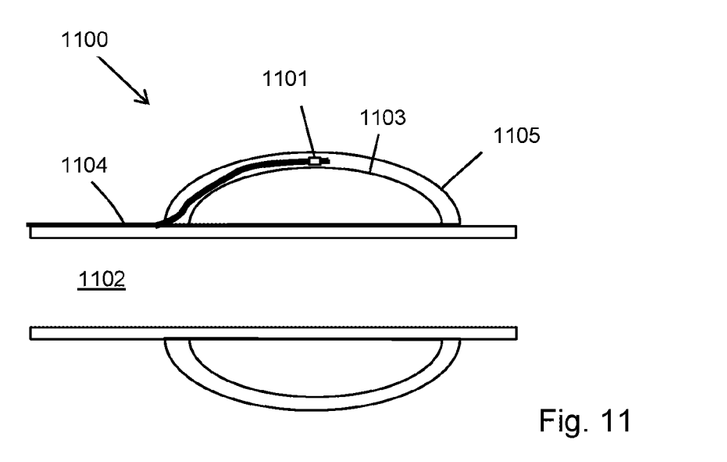
FIG. 11 is a schematic diagram of a distal end portion of a further alternative exemplary airway maintenance device.

FIG. 11 illustrates the distal end of an alternative example of an airway maintenance device 1100 comprising a lumen 1102. Airway maintenance device 1100 comprises an optical fibre pressure sensor 1101 formed in an optical fibre 1104. Optical fibre pressure sensor 1101 is incorporated into, and located on the surface of, a first inflatable cuff 1103. A second inflatable cuff 1105 surrounds the first inflatable cuff 1103 such that the optical fibre pressure sensor 1101 is sandwiched between the first and second cuffs 1103, 1105. The pressure sensor 1101 may be a pressure sensor according to any previous embodiment, including a Fabry-Pérot cavity, fibre Bragg grating, and a plurality of pressure sensors. Alternatively or additionally, the airway maintenance device 1100 may comprise an optical sensor for measuring blood flow, such as those described above, sandwiched between the first and second cuffs.

The second, or outer, cuff 1105 may provide protection to the pressure and/or optical sensor positioned between the first, or inner, cuff 1103 and the second 1105 cuff. There may also be more flexibility in choosing a location of the pressure and/or optical sensor than in embodiments without a second cuff 1105. The pressure and/or optical sensor may be attached to the first cuff 1103 and/or the second cuff 1105.

Figure 12A:
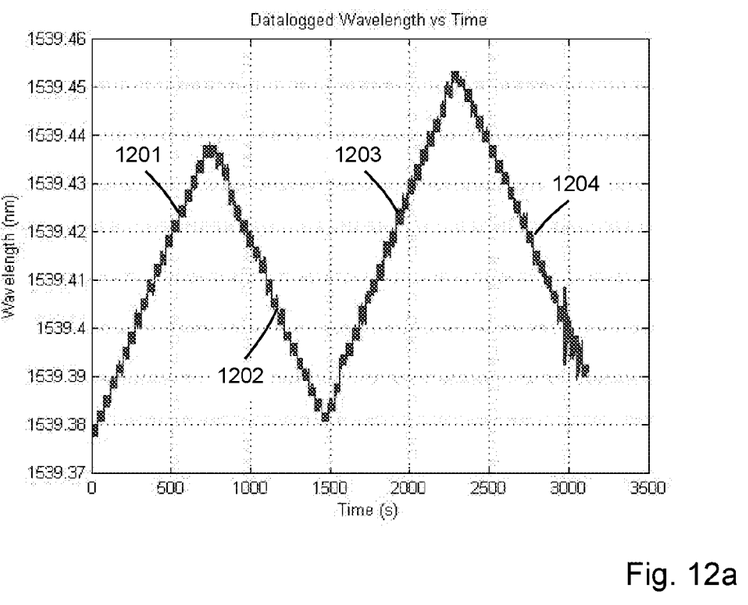
FIG. 12a is a plot of the measured wavelength of reflected light as a function of time during the application of pressure to a sensor.
Figure 12B:
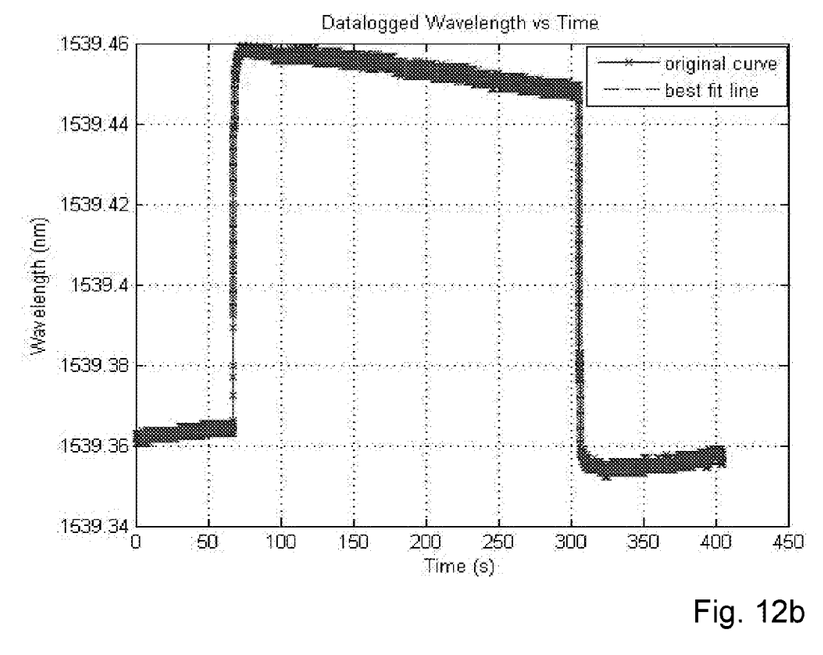
FIG. 12b is a plot of the measured wavelength of reflected light as a function of time showing the stability of the wavelength shift.
Figure 13:
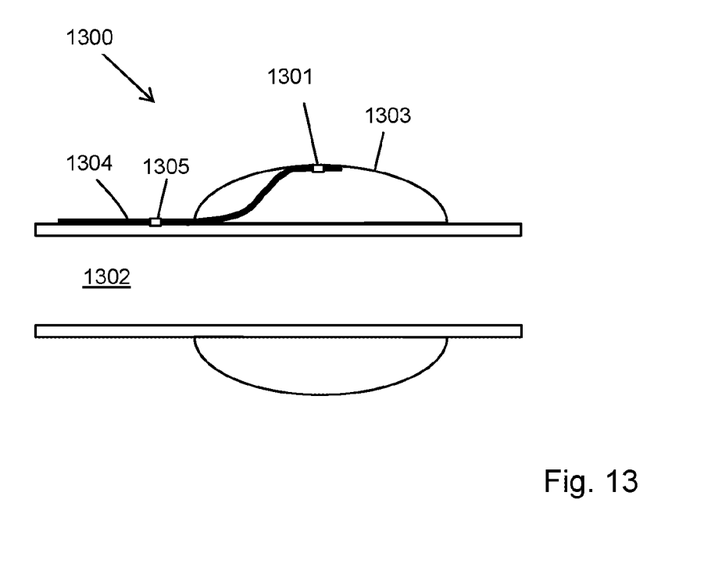
FIG. 13 is a schematic diagram of a distal end portion of a further alternative exemplary airway maintenance device.

FIGS. 12 and 13 illustrate the results of measurements of fibre Bragg grating sensors encapsulated into patches.

FIG. 12a illustrates the wavelength of reflected light from a single FBG patch as a function of time during loading and unloading of a pressure. In a first loading region 1201, a pressure gradient of 0.5842 kPa/s was applied to the patch. The gradient of the shift in reflected light because of this pressure gradient was $1.2286 \times 10^{-3}$ nm/s, giving a sensitivity of $2.1 \times 10^{-3}$ nm/kPa. In a first unloading region 1202, the pressure was unloaded with a gradient of 0.5728 kPa/s. The gradient of the shift in reflected light because of this pressure gradient was $1.2773 \times 10^{-3}$ nm/s, giving a sensitivity of $2.23 \times 10^{-3}$ nm/kPa. In a second loading region 1203, a pressure gradient of 0.6077 kPa/s was applied to the patch. The gradient of the shift in reflected light because of this pressure gradient was $1.285 \times 10^{-3}$ nm/s, giving a sensitivity of $2.11 \times 10^{-3}$ nm/kPa. In a second unloading region 1204, the pressure was unloaded with a gradient of 0.5781 kPa/s. The gradient of the shift in reflected light because of this pressure gradient was $1.2673 \times 10^{-3}$ nm/s, giving a sensitivity of $2.19 \times 10^{-3}$ nm/kPa.

FIG. 12b illustrates the stability of the shift in wavelength of reflected light due to an applied pressure over time.

Figure 14:
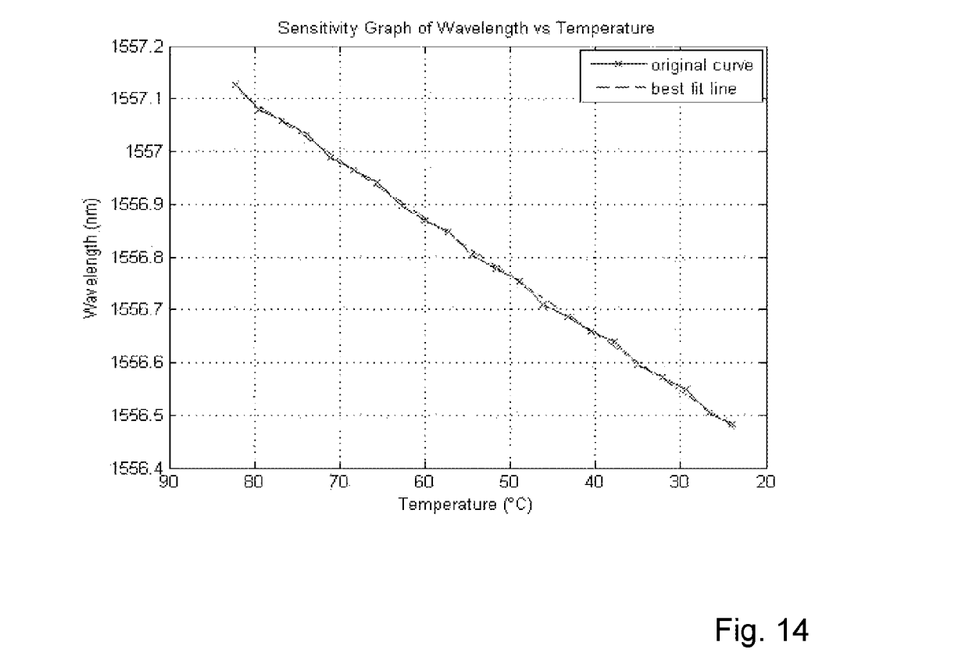
FIG. 14 is a plot the measured wavelength of light reflected from a temperature sensor as a function of temperature.

FIG. 13 illustrates an alternative embodiment of the distal end of an airway maintenance device 1300 comprising a lumen 1302. Airway maintenance device comprises a sensor 1301 incorporated into a cuff 1303. Sensor 1301 may be one or more of any of the sensors described above. Device 1300 further comprises a temperature sensor 1305. In the illustrated embodiment, temperature sensor 1305 is a fibre Bragg grating. The wavelength of light reflected from the grating may shift depending on the temperature of the grating. The sensitivity of the reflected light to temperature of a test fibre Bragg grating is shown in FIG. 14. Thus a fibre Bragg grating can be used to measure temperature similarly to measuring pressure. Positioning an FBG sensor out of the cuff region also allows for temperature effects to be compensated for during measurements, assuming that the temperature of the sensors is similar when in use.

In the illustrated embodiment, temperature sensor 1305 is formed in the same optical fibre 1304 as sensor 1301, but is not incorporated into the cuff 1303. In alternative embodiments, the temperature sensor 1305 may be formed in a different optical fibre to sensor 1301, and/or may be incorporated into the cuff 1303. Device 1300 may further comprise a second cuff, similar to the second cuff of the embodiment illustrated in FIG. 11.

Figure 15:
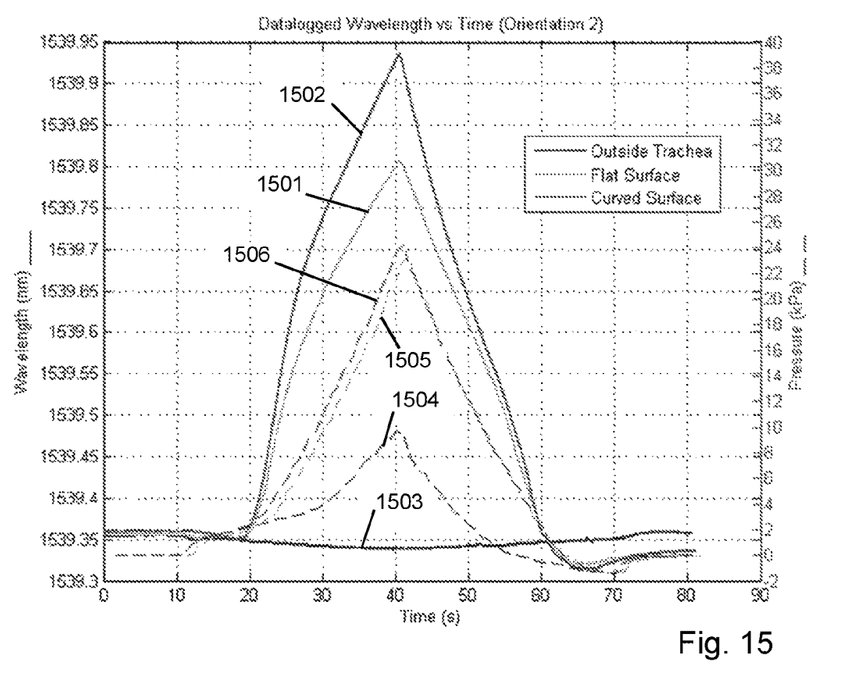
FIG. 15 is a plot of wavelength shift and intracuff pressure as a function of time for FBG sensors in an outside of a modeled trachea.
Figure 16:
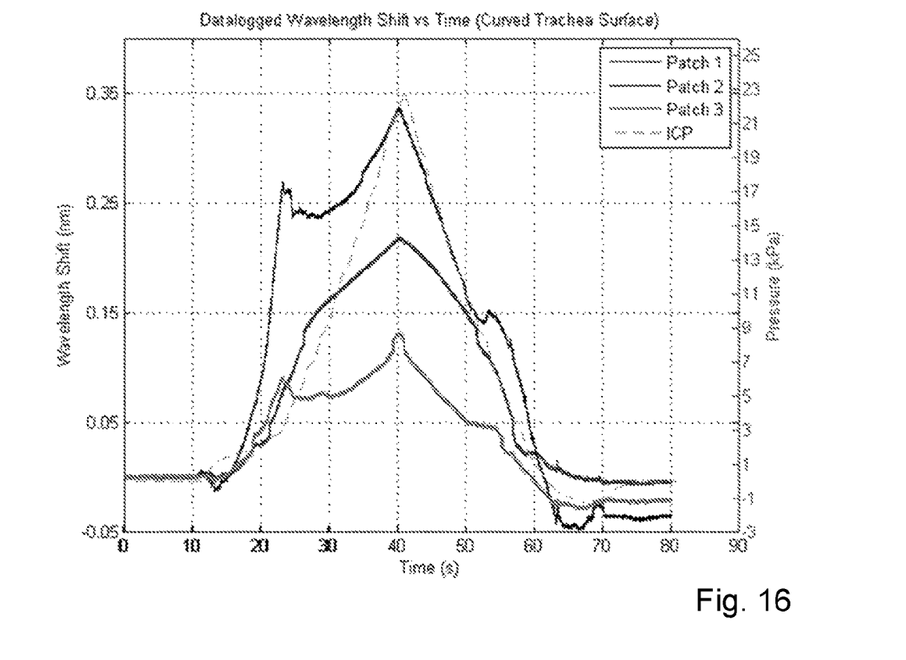
FIG. 16 is a plot of wavelength shift and intracuff pressure as a function of time for FBG sensors in three patches.

FIGS. 15 and 16 show experimental data from FBG sensors on an inflatable cuff positioned within an artificial trachea. FIG. 15 shows the variation in pressure measurements for a flat surface 1501 (similar to the trachealis muscle region at the posterior of the trachea) compared to a curved surface 1502 (the remaining region, including the anterior of the trachea), and in comparison to measurements taken outside the trachea 1503, i.e. with the cuff inflated without being in contact with the modeled trachea. Pressure measurements (dotted lines, right hand scale, for outside trachea 1504, flat surface 1505 and curved surface 1506) correlate well with wavelength shift measurements (solid lines, left hand scale), with a curved surface tending to produce a higher wavelength shift for the same intracuff pressure.

FIG. 16 shows the variation in wavelength shift (solid lines, left hand scale) over time for three different patch positions in an experimental cuff within a modeled trachea, with intracuff pressure (dotted line, right hand scale) shown for comparison. Wavelength shift measurements correlate with pressure, although tend to show more variation, probably due to measuring contact pressure that can vary depending on the degree of contact of the cuff with the trachea wall. As mentioned above, the optimal position for a patch tends to be in the middle of the cuff, although using multiple patches positioned at different positions along the cuff can be advantageous to account for and measure different contact pressures along the cuff.

An airway maintenance device incorporating both a capillary blood flow sensor and an intracuff or tracheal contact pressure sensor of the types outlined above, enables continuous monitoring of the microcirculation, intracuff and applied pressure, thereby providing information on the vitality of the tissues during intubation. This allows intensivists, neonatologists, anaesthetists and others to actively protect their patients from harm by manipulating the key variables for each patient, rather than by applying inflexible guidelines that in some cases can result in harm to the patient.

Other embodiments are intentionally within the scope of the invention as defined by the appended claims.

REFERENCES

1. J. E. Spiegel, "Endotracheal Tube Cuffs: Design and Function", Anesthesiology News, Guide to Airway Management, 2010, pp 51-58.
2. Pneumatikos et al, "Ventilator-associated Pneumonia or Endotracheal Tube-associated Pneumonia?" Anesthesiology 2009; 110:673-80
3. US 2012/0089041 (see also US 2012/0089023)
4. US 2011/0030694
5. US 2004/0003814
6. US 2010/0006103
7. WO 2004/030527
8. U.S. Pat. No. 5,005,573
9. J. Brimacombe et al., "Direct measurement of mucosal pressures exerted by cuff and non-cuff portions of tracheal tubes with different cuff volumes and head and neck positions", British Journal of Anaesthesia 82(5): 708-11 (1999)
10. G. T. G. Knowlson & H. F. M. Basset, "The pressures exerted on the trachea by endotracheal inflatable cuffs", British Journal of Anaesthesia 42, 834-837, 1970
11. P. Goethals et al., "A novel airway device with tactile sensing capabilities for verifying correct endotracheal tube placement", J Clin Monit Comput (2014) 28: 179-185
12. E. Bick et al, "Fewer sore throats and a better seal: why routine manometry for laryngeal mask airways must become the standard of care", Anaesthesia 2014, pp 1-5.

The invention claimed is:

1. An apparatus comprising:
   an airway maintenance device comprising an airway lumen having a proximal end and a distal end, and a distal end portion comprising an inflatable cuff incorporating an optical sensor configured to measure capillary blood flow rate in tissue surrounding the distal end when in position within a patient's airway, wherein the optical sensor comprises a portion of an optical fibre extending to the distal end portion along the lumen; and
   a control unit connectable to the optical sensor, the control unit configured to determine a measure of the capillary blood flow rate from a signal received from the optical sensor, wherein the control unit comprises:
      a light source configured to transmit light along the optical fibre to the optical sensor; and
      a light detector configured to measure light received in the signal from the optical sensor along the optical fibre,
      the control unit being configured to determine the measure of the capillary blood flow rate from an intensity of light received from the optical sensor.
2. The apparatus of claim 1 wherein the portion of the optical fibre is at a distal end of the optical fibre.
3. The apparatus of claim 1 wherein the portion of the optical fibre has a modified cladding such that light passing along the optical fibre from the proximal end exits the optical fibre through the modified cladding.
4. The apparatus of claim 1 wherein the optical fibre has a distal end face arranged to allow light passing along the optical fibre from the proximal end to exit the optical fibre through the distal end face.
5. The apparatus of claim 1 wherein the portion of the optical fibre has a radius of curvature below a minimum bend radius of the optical fibre such that light travelling within the optical fibre is emitted from the portion of the optical fibre.
6. The apparatus of claim 1 wherein the optical sensor comprises distal end portions of a pair of said optical fibres, a first optical fibre comprising a light emitting portion and a second optical fibre comprising a light detecting portion.
7. The apparatus of claim 6 comprising a reference optical fibre having a reflective end face.
8. The apparatus of claim 6 wherein the light emitting portion and the light detecting portion are offset relative to each other.
9. The apparatus of claim 6 comprising an optically opaque barrier between the light emitting portion of the first optical fibre and the light detecting portion of the second optical fibre.
10. The apparatus of claim 1 wherein the airway maintenance device is an endotracheal tube, a tracheostomy tube or a supraglottic airway device.
11. The apparatus of claim 1 comprising an additional sensor configured to measure pressure, temperature and/or humidity at the distal end of the airway lumen.
12. The apparatus of claim 11 wherein the additional sensor is a fibre optic pressure sensor.
13. The apparatus of claim 1 wherein the light source and light detector are configured to respectively transmit and detect green light.
14. The apparatus of claim 1 wherein the inflatable cuff is configured to provide a fluid seal between the inflatable cuff and the patient's trachea when inflated.

* * * * *